(12) United States Patent
Faccioli et al.

(10) Patent No.: US 9,016,925 B2
(45) Date of Patent: Apr. 28, 2015

(54) MIXER FOR BIPHASIC COMPOUNDS

(75) Inventors: Giovanni Faccioli, Monzambano (IT); Renzo Soffiatti, Nogara (IT)

(73) Assignee: Tecres S.p.A., Sommacampagna (Verona) (IT)

( * ) Notice: Subject to any disclaimer, the term of this patent is extended or adjusted under 35 U.S.C. 154(b) by 0 days.

(21) Appl. No.: 13/148,185

(22) PCT Filed: Feb. 6, 2009

(86) PCT No.: PCT/IB2009/000220
§ 371 (c)(1),
(2), (4) Date: Aug. 24, 2011

(87) PCT Pub. No.: WO2010/089622
PCT Pub. Date: Aug. 12, 2010

(65) Prior Publication Data
US 2012/0092951 A1 Apr. 19, 2012

(51) Int. Cl.
*B01F 5/12* (2006.01)
*B01F 13/00* (2006.01)
*B01F 11/00* (2006.01)
*B01F 15/00* (2006.01)
*B01F 15/02* (2006.01)
*A61F 2/46* (2006.01)
*B01F 7/00* (2006.01)

(52) U.S. Cl.
CPC ......... *B01F 13/002* (2013.01); *A61F 2002/469* (2013.01); *A61F 2002/4693* (2013.01); *B01F 7/00291* (2013.01); *B01F 7/00341* (2013.01); *B01F 11/0054* (2013.01); *B01F 13/0023* (2013.01); *B01F 15/00467* (2013.01); *B01F 15/00506* (2013.01); *B01F 15/0205* (2013.01); *B01F 15/0206* (2013.01); *B01F 15/0225* (2013.01); *B01F 15/027* (2013.01); *B01F 15/0278* (2013.01)

(58) Field of Classification Search
CPC ..................................................... B01F 13/002
USPC ....................... 366/130, 176.3, 189, 256, 290
See application file for complete search history.

(56) References Cited

U.S. PATENT DOCUMENTS

| 2,831,606 | A | * | 4/1958 | Alters | 222/1 |
| 2,908,555 | A | * | 10/1959 | Grosskopf | 422/86 |
| 3,570,486 | A | * | 3/1971 | Engelsher et al. | 604/88 |
| 3,618,216 | A | * | 11/1971 | Jaeger | 433/90 |
| 3,724,077 | A | * | 4/1973 | Preston et al. | 433/90 |
| 4,272,479 | A | * | 6/1981 | Huneke et al. | 422/413 |
| 4,300,910 | A | * | 11/1981 | Pannwitz | 436/102 |
| 4,686,192 | A | * | 8/1987 | Fisher | 436/60 |
| 5,193,907 | A | * | 3/1993 | Faccioli et al. | 366/130 |
| 5,297,698 | A | * | 3/1994 | Martin | 222/95 |

(Continued)

FOREIGN PATENT DOCUMENTS

| DE | 195 32 015 A1 | 3/1997 |
| EP | 0 266 058 A2 | 5/1988 |

(Continued)

*Primary Examiner* — Walter Griffin
*Assistant Examiner* — Abbas Rashid
(74) *Attorney, Agent, or Firm* — Tutunjian & Bitetto, P.C.

(57) ABSTRACT

Mixer for biphasic compounds, including a chamber for containing a solid phase and a cartridge containing a phial of a liquid phase, said chamber and said cartridge being able to communicate through respective channels, wherein said cartridge includes an external casing made in a deformable material and said phial is of the breakable type.

6 Claims, 8 Drawing Sheets

(56) References Cited

U.S. PATENT DOCUMENTS

| | | | |
|---|---|---|---|
| 5,876,116 A * | 3/1999 | Barker et al. | 366/182.3 |
| 6,116,773 A * | 9/2000 | Murray | 366/139 |
| 6,984,063 B2 * | 1/2006 | Barker et al. | 366/139 |
| 7,018,089 B2 * | 3/2006 | Wenz et al. | 366/130 |
| 8,038,682 B2 * | 10/2011 | McGill et al. | 606/94 |
| 8,220,985 B2 * | 7/2012 | Barger et al. | 366/257 |
| 2003/0103410 A1 * | 6/2003 | Scheying | 366/195 |
| 2005/0105384 A1 * | 5/2005 | Eder et al. | 366/139 |
| 2005/0105385 A1 * | 5/2005 | McGill et al. | 366/139 |
| 2005/0281132 A1 | 12/2005 | Armstrong et al. | |

FOREIGN PATENT DOCUMENTS

| | | | |
|---|---|---|---|
| EP | 1 031 333 A1 | 8/2000 | |
| EP | 1 466 572 A2 | 10/2004 | |
| WO | WO2004002375 | 1/2004 | |
| WO | 2004/069396 A1 | 8/2004 | |
| WO | 2005/018830 A2 | 3/2005 | |
| WO | WO2006123205 | 11/2006 | |
| WO | WO 2007/000631 * | 1/2007 | B01F 13/00 |
| WO | 2008/045329 A2 | 4/2008 | |

* cited by examiner

US 9,016,925 B2

MIXER FOR BIPHASIC COMPOUNDS

TECHNICAL FIELD OF THE INVENTION

The invention relates to a mixing device for biphasic compounds, particularly biphasic compounds used in the arthroplasty field for reconstructing or filling bone structures.

BACKGROUND ART

At present mixers are known which mix a liquid phase with a solid phase in order to make the biphasic compound to dispense.

The known types of mixers can provide, for this purpose, a phial with the liquid phase connectable to a syringe containing the solid phase.

To use, the liquid contained in the phial is put into the syringe inside which a stirring device mixes the compound.

All these operations, i.e. putting the liquid phase into the syringe and mixing, must be done under sterile conditions, i.e., with no direct contact with the outside.

For this reason, in the known mixers, the phial is positioned inside a container and to get the liquid out without any direct manual contact, devices are used that can be maneuvered from outside and designed to break the phial.

The liquid that comes out of the phial must then be put inside the syringe by means of suitable pouring means that transfer the liquid from the phial container to the mixing syringe.

A mixer of this type is described in the patent application VI2005A000152 filed by the same applicant. Such known mixers have been found to be effective from the point of view of sterility of the operations but, however, they do have some drawbacks connected to the relative difficulty in the phial breaking phase and transferring the liquid into the syringe which renders the device slightly complicated.

Another aspect of the known types of mixer concern the next phases of compound preparation during which, once the liquid and solid phases have come together in the syringe, the compound must be mixed by means of suitable stifling devices until a compound is obtained which is then dispensed, acting on the syringe piston. From this aspect, the known types of mixer have some drawbacks linked to the construction difficulty in fitting the syringe with effective stirring means to stir the compound and that has an accurate and controlled dispensing of the finished compound.

It should also be noted that, since arthroplasty operations are usually done via radioscopy with the known risks of exposure to radiations that the operators are subject to, the need is now felt to dispense the compound according to procedures that allow such risks to be minimised.

A dispenser of the type known is described as an example in the application VI2002A000140 in the name of the same applicant.

SUMMARY OF THE INVENTION

The technical aim of this invention is therefore, to provide a mixing device that allows the mixing of the liquid and solid phases, easily and in a sterile environment.

Within the scope of this technical aim, one such object of this invention is to provide a mixer for biphasic compounds that has a simple and reliable structure but which is also capable of effectively mixing the phases of the compound and dispensing the finished compound in a controlled and accurate manner.

Another object of this invention is to provide a mixer for biphasic compounds that can be effectively controlled remotely to dispense the compound necessary for arthroplasty operations.

This aim and these objects are all achieved with a mixer according to one or more of the claims enclosed.

A first advantage of the invention is that the operations of bringing the two phases together and the mixing and dispensing of the compound are obtained with a device that is relatively simple and easy to use.

A second advantage is that all the operations are done avoiding the direct contact with the outside environment.

Yet another advantage is that the mixer according to the invention allows the times to be reduced needed for mixing and dispensing the compound.

Another advantage is that the mixer according to the invention allows dispensing of the exact doses of the compound in a controlled and accurate manner.

Another, but certainly not the last, advantage is that the mixer according to the invention allows the compound to be dispensed according to operating methods that minimize all possible radiation exposure risks of the operators who are performing the arthroplasty surgery operation.

BRIEF DESCRIPTION OF THE DRAWINGS

These and other advantages can be better understood by all technicians in the sector thanks to the description that follows and the annexed drawings given as an example but which are not limiting, wherein.

DETAILED DESCRIPTION OF PREFERRED EMBODIMENTS

With reference to the drawings, 1 designates a mixer for biphasic compounds according to the invention in one of its embodiments.

The mixer 1 of biphasic compounds according to the invention comprises one mixing unit, indicated with 3, one dispensing unit, indicated with 2 and one cartridge, indicated with 4, containing the liquid phase and which can be connected together in order to mix the liquid phase with the solid phase and to dispense a quantity of the mixed biphasic compound.

Figure 1:
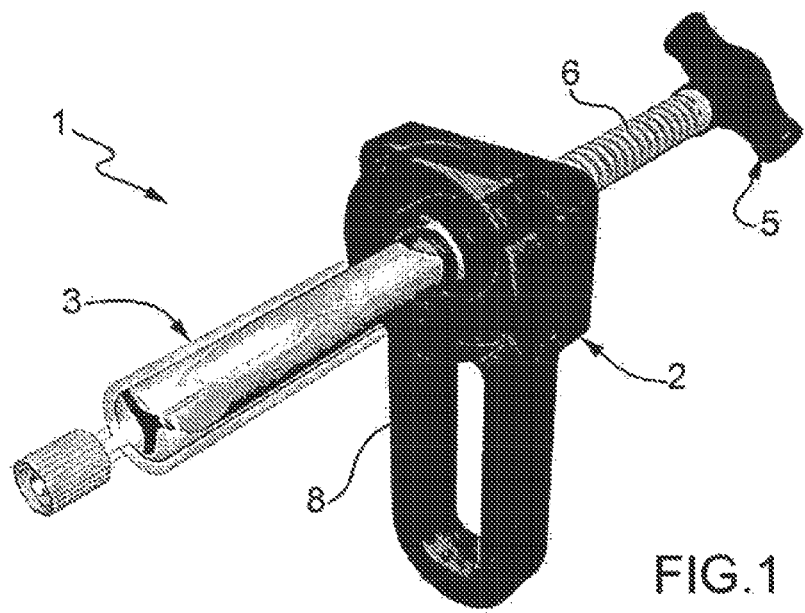
FIG. 1 shows a perspective view of a mixer according to the invention with one mixing unit and one dispensing unit operatively connected.
Figure 2:
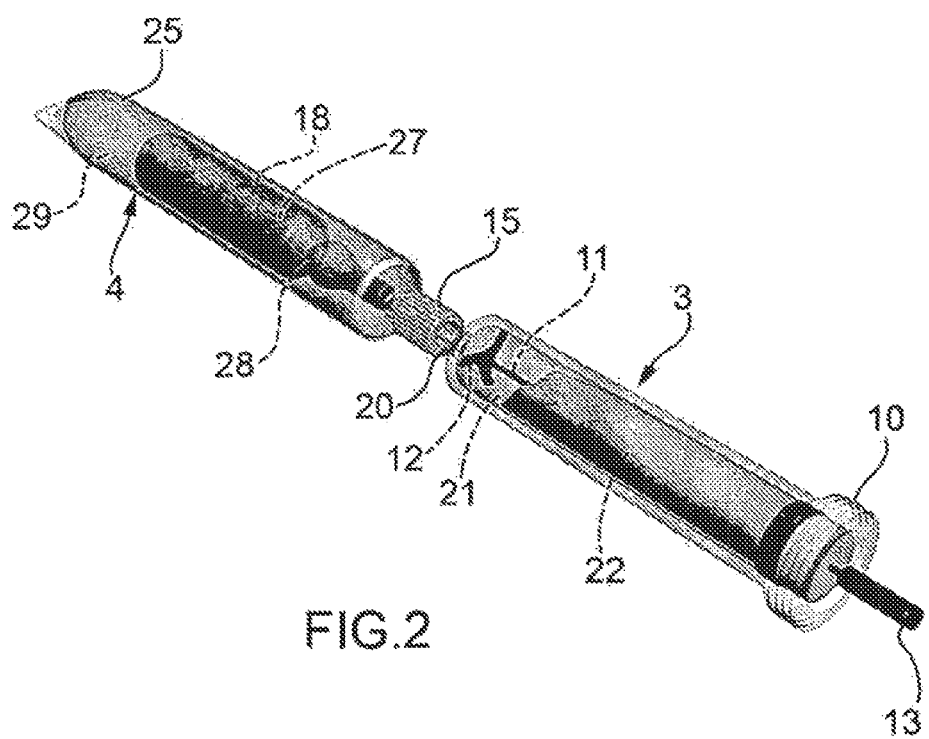
FIG. 2 shows a perspective view of a detail of one mixing unit connected to a cartridge according to the invention containing the liquid phase.
Figure 3:
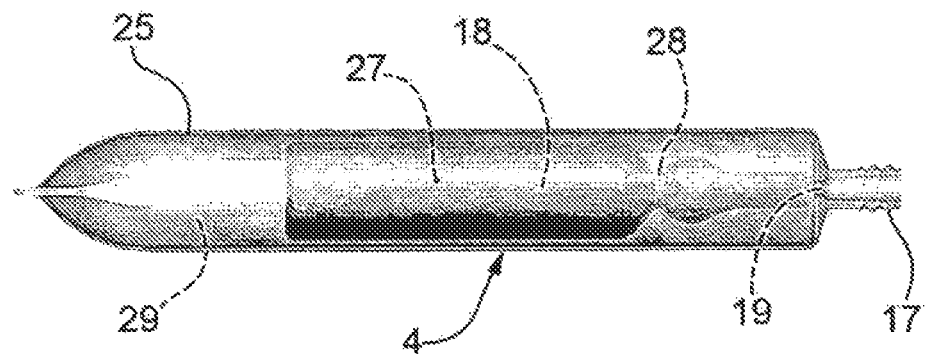
FIG. 3 shows a detail of the cartridge of FIG. 2.

In more detail, and in particular with reference to FIGS. 2 and 3, the mixer 1 comprising a chamber 21 for containing a solid phase 22, and a cartridge 4 containing a phial 18 of a liquid phase.

The chamber 21 and the cartridge 4 can communicate through the relative channels 19, 20 and can be joined in a removable manner, e.g. using screw means composed of an external thread 17 made by the channel 19 of the cartridge 4 and which engages with an internal thread 16 of a locking ring nut 15 turning around the channel 20 of the mixing chamber 21.

According to the invention, the cartridge 4 advantageously comprises an external casing 25 made in a deformable material so that the phial 18, being the breakable type, once connected to the chamber 21, can be broken from the outside, e.g. on a breaking point 28, according to the method of the type known.

When the phial has been broken the deformable casing can then be squeezed and the liquid transferred inside the chamber 21 through the channels 19 and 20, preferably interposing a filter—not shown in the figures—to prevent any fragments of glass from accidentally getting inside the chamber 21.

Advantageously, with this technical solution, the liquid phase is joined with the solid phase inside the chamber 21 simply, in a completely sterile fashion and with no contact with the outside and without the minimum mechanical or structural complication.

It is also preferable that the casing 25 is made in a flexible material—that is, that acts substantially in an elastic way and has an internal volume 29 greater than the volume taken up by said phial 18.

With this solution it is possible to exploit an advantageous pumping effect to force the liquid into the chamber 21 without having to provide other or more complicated auxiliary devices.

Figure 4:
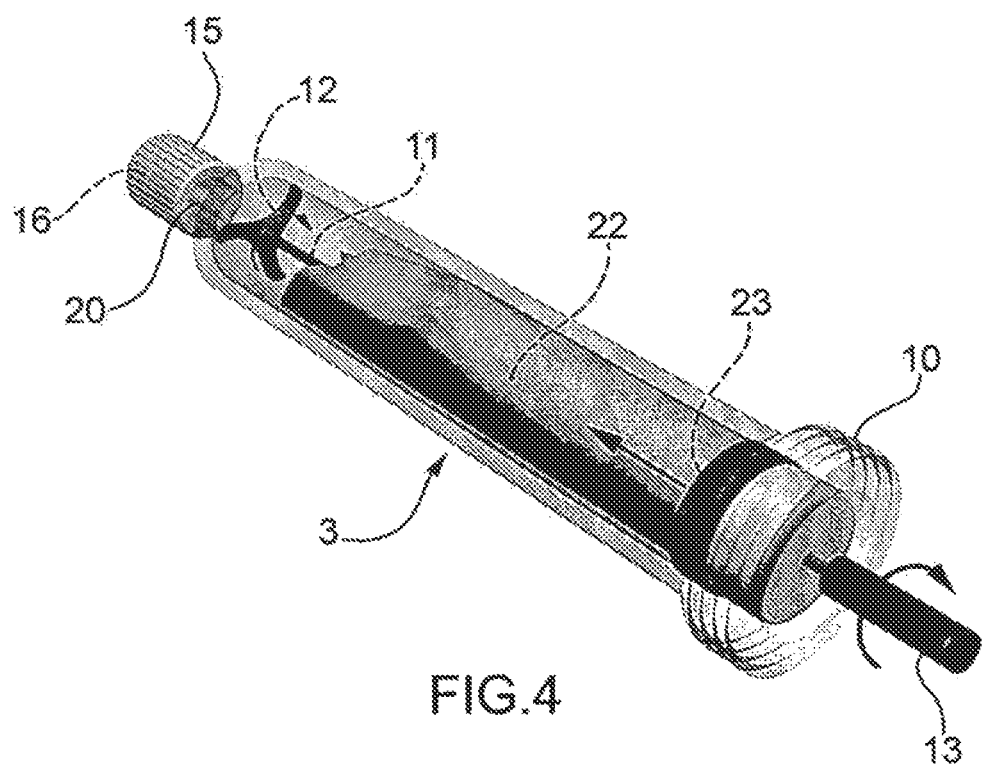
FIG. 4 shows a detail of the mixing unit of FIG. 2.
Figure 5:
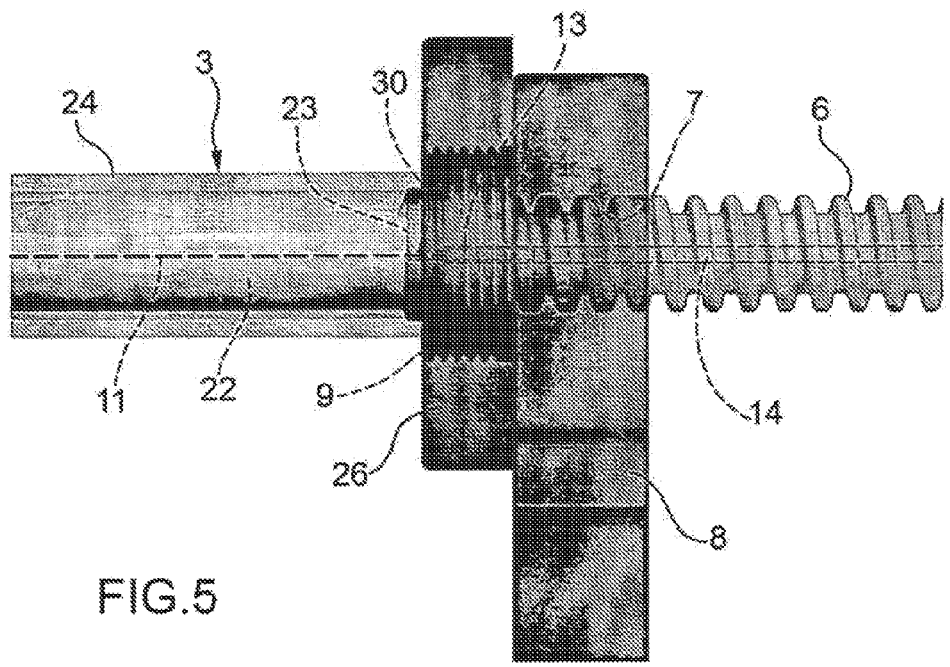
FIG. 5 shows a detail of the connection between the mixing unit and the dispensing unit of FIG. 1.

With particular reference to FIGS. 4 and 5, the mixing unit 3 and the dispensing unit 2 according to the invention are described in more detail.

In the form of embodiment described here, the unit 3 is in the shape of a syringe body comprising a container 24 defining inside it the mixing chamber 21, and which has on one end the channel 20 already described that has a ring nut 15 for fixing to the cartridge 4.

On the other end, the container 24 has a piston 23 which seals the chamber 21 and fixing means 10 for fixing to the dispensing unit 2 which, in the form of embodiment illustrated, are composed of an external screw 10 which engages frontally with an internal screw 9 made in one block 26 integral with the handgrip 8 of the unit 2 which is described in more detail further on.

In different forms of embodiment, the mixing unit 3 and the dispensing unit 2 can in any case be connected by removable means of different kinds either quick coupling or interlocking like, e.g., a bayonet coupling or a similar type.

According to the invention, stifling means are arranged inside the chamber 21 which, in the form of embodiment described, comprise a stirrer 12 in the shape of a propeller driven by a longitudinal rod 11 that extends at least along the whole chamber 21, going through a hole 30 of the piston 23 and which is hermetically sealed.

Preferably, the rod 11 also comprises a gripping knob 13 which extends beyond the chamber 21 and which facilitates the propeller 12 maneuvering.

Note that use of the knob is advantageous but is not essential, for example when one wishes to use a connection between the mixing unit 3 and the dispensing unit 2 of the lateral snap-in type, e.g. composed of a prismatic coupling (e.g. dovetail) achieved by the transversal movement with respect to a longitudinal axis of the mixer (e.g. the axis of the screw 6 and/or of the chamber 21).

Figure 6:
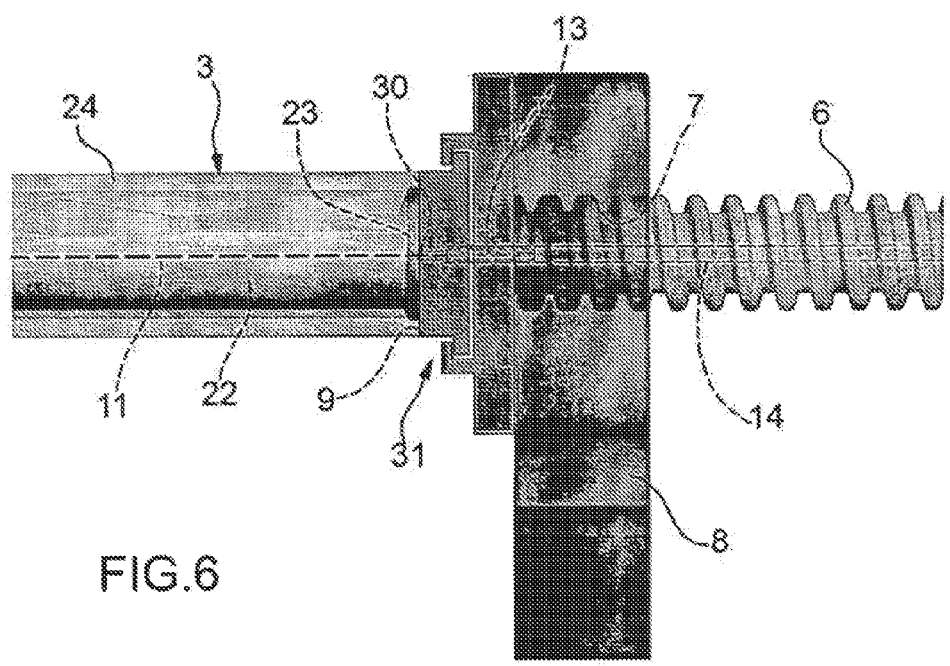
FIG. 6 shows schematically a lateral snap-in connection between the mixing unit and the dispensing unit.

One possible example of a lateral snap-in connection 31 is schematized in FIG. 6.

When using, the stirrer 12 can be turned and moved longitudinally by means of the rod 11 which slides through the piston 23 until completing the mixing of the solid phase which is inside the chamber 21 with the liquid phase already in the cartridge 4 and until a biphasic compound is obtained, ready for final dispensing.

Advantageously, the dispensing phase is carried out by means of a dispensing unit 2 that comprises an extrusion screw with an external thread 6 that engages with a corresponding internal thread 7 created inside the handgrip 8 so as to advance, subsequent to the rotation of the screw, e.g. by using the knob 5.

Subsequent to rotation, the screw 6 moves forward and presses on the piston 23 forcing it to slide along the mixing chamber 21.

According to the invention, the screw 6 has a longitudinal inner cavity 14 that houses the rod 11 in a sliding manner, so that as the screw and piston advance the rod 11 returns and is concealed inside the cavity 14 without interfering with the dispensing action made by the unit 2.

With this solution an effective mixing of the compound has been achieved and, without any delay, to be able to dispense in a controlled and accurate way, the quantity wanted of the compound, all under conditions of maximum sterility and absence of manipulations or possible contact of the compound with the outside.

In another form of embodiment of the mixer for biphasic compounds according to the invention, represented in FIGS. 7 to 13, the mixing unit 3 comprises a container 24, substantially, in the shape of a syringe, defining the mixing chamber 21 and communicating, on one of its ends, with the channel 20. The screw means, described previously, are also on this same end for the removable connection to the cartridge 4.

Figure 7:
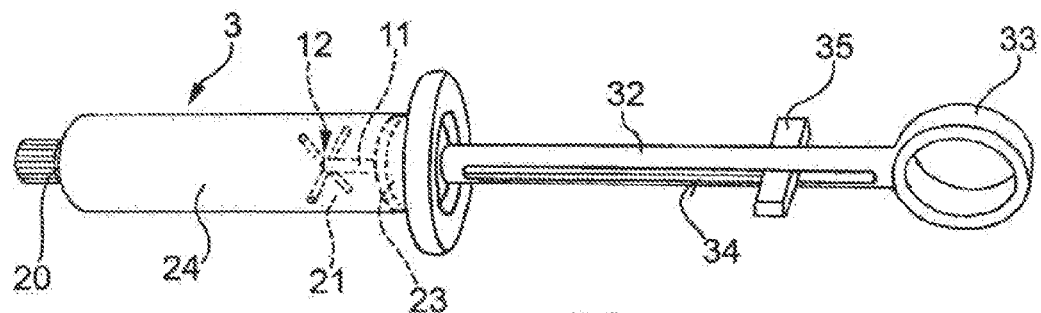
FIG. 7 illustrates a perspective view of the mixing unit in another form of embodiment of the mixer according to the invention.

Reference is now made to FIG. 7 in particular. Where the other end is, the container 24 is associated with a piston 23 which closes (thus sealing) the mixing chamber 21 to which a manually operated stem 32 is integrally connected, used to dispense the compound, as is more clearly explained below. In particular, the stem 32 has, on its free end, an eyelet 33 for manual thrusting, or alternatively for being connected to thrusting means which are not represented in the figures enclosed: the thrust exerted on the eyelet 33 does, of course, allow the compound to be dispensed through the channel 20.

The stem 32 is hollow inside and its axial cavity communicates with the hole 30 of the piston 23. In the axial cavity of the stem 32 the rod 11 is engaged in a sliding manner and has the stirrer 12 for mixing the compound on its end. The stem 32 also has a pair of opposing longitudinal slots 34 that communicate with its axial cavity and along which a sort of handgrip 35 is guided in a sliding manner: the latter comes out from said slots 34 sideways and allows the rod 11 to move inside the chamber 21 to mix the compound.

Figure 8:
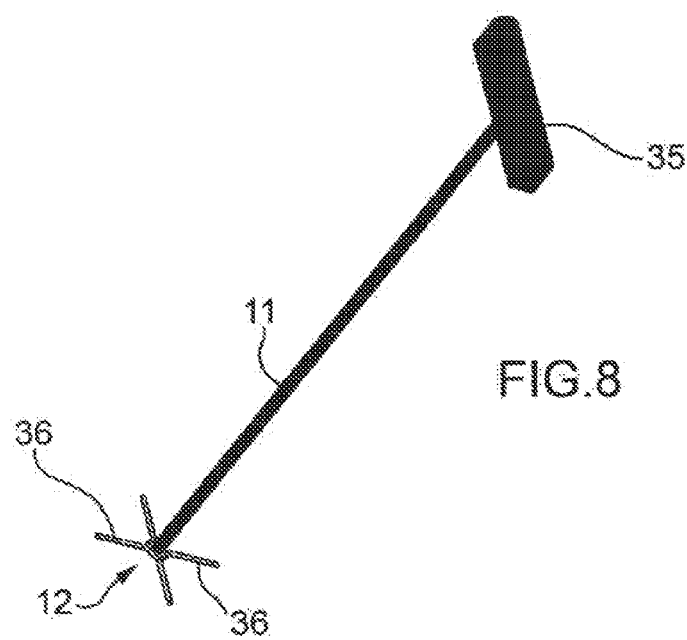
FIG. 8 represents a perspective view of the stirrer of the mixing unit of FIG. 7.

The stirrer 12, represented in particular in FIG. 8, comprises a propeller, with a substantially cross shape, where the four blades 36 have an even cross section and smaller compared to that provided in the previous form of embodiment: this solution is even more effective in association with a mixing unit 3 like the one described previously and that can even be quite big. In such a situation therefore, the small dimensions of the blades 36 of the stirrer 12 limit resistance to stifling which the operator is aware of and feels especially when the compound being prepared has a relatively high viscosity.

Figure 9:
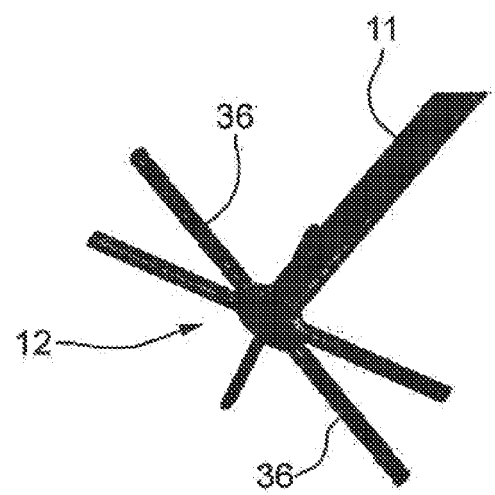
FIG. 9 shows a perspective view of another form of embodiment of the stirrer of the mixing unit of FIG. 7.

In one of its alternative forms of embodiment, represented in FIG. 9, the stirrer 12 is composed of a propeller comprising six blades for applications in which the compound to be prepared has a relative low viscosity.

Figure 10:
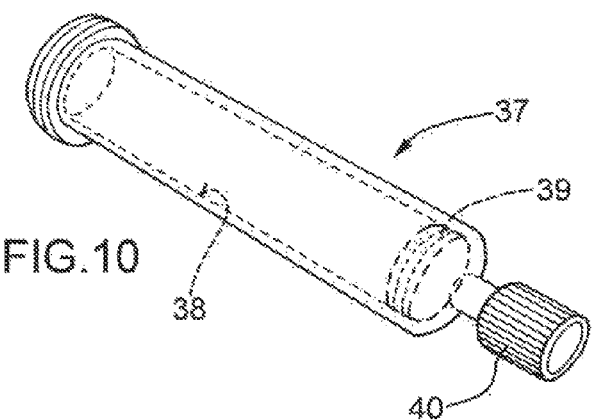
FIG. 10 illustrates a perspective view of a syringe being used associable with the mixing unit of FIG. 7.

In addition, the mixer, according to this current form of embodiment, comprises at least one syringe, indicated with 37 and represented in FIG. 10, usable for dosing the quantity of compound to use in each arthroplasty operation. The syringe 37 is, in fact, smaller compared to the mixing unit 3 and in particular it substantially corresponds to the dose required for each operation.

The syringe 37 has an internal dispensing volume 38 delimited by a dispensing piston 39, sliding freely and sealed. On one of its ends the syringe 37 has screw elements 40 for the removable and sealed connection to the ring nut 15 of the mixing unit 3, e.g. composed of an external thread on this same end; in addition, the screw elements 40 can comprise, in an equal measure and whenever demanded by application requirements, a sealed fixing ring nut.

The way in which the mixer is used according to this form of embodiment is the following.

Figure 11:
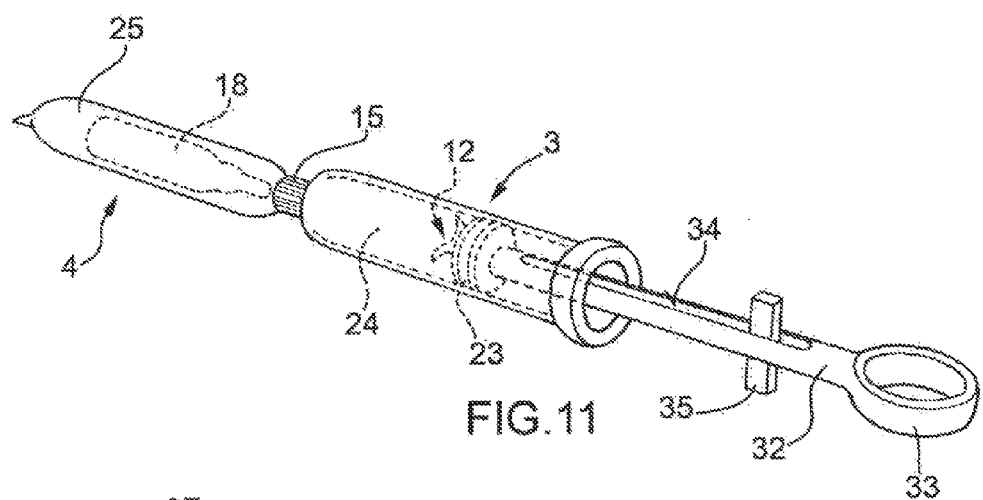
FIG. 11 represents a perspective view of the mixing unit of FIG. 7 coupled to the cartridge containing the liquid phase of the compound.

Once the mixing unit 3 is ready with the solid phase of the compound and the cartridge 4 with the liquid phase of the compound, they are connected together with the screw means 15 as illustrated in FIG. 11. After this the phial 18 must be broken and then the casing 25 squeezed to push the liquid phase inside the chamber 21. When all the liquid phase has been pushed inside the chamber 21, operate the handgrip 35 of the stirrer 12 manually so the stirrer 12 moves axially and alternatively inside the chamber 21, mixing the two phases and obtaining the compound required.

Figure 12:
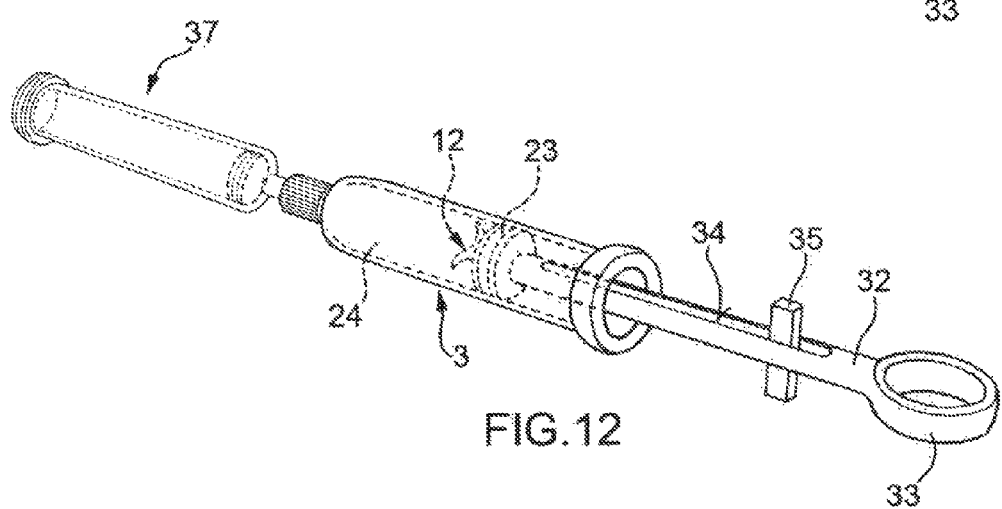
FIG. 12 shows a perspective view of the mixing unit of FIG. 7 coupled to the syringe being used.
Figure 13:
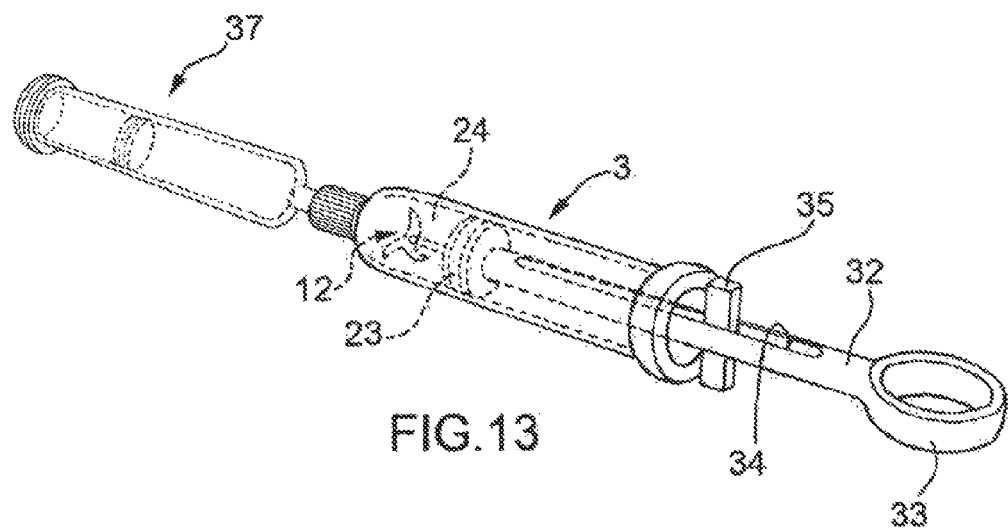
FIG. 13 illustrates a perspective view of the mixing unit of FIG. 7 in the phase of compound dispensing inside the syringe being used.

Now, to achieve the exact dosage of the quantity of compound to use in an arthroplasty operation, separate the casing 25, emptied of its contents, from the mixing unit 3 and connect the syringe 37 described previously to the mixing unit 3, using the screw elements 40 as shown in FIG. 12. Lastly, operate on the eyelet 33 of the mixing unit 3, exerting sufficient manual pressure so as to transfer a certain quantity of the compound from the chamber 21 to the dispensing volume 38, as can be seen in FIG. 13: the quantity of compound transferred will, of course, be defined by the dispensing volume 38 itself and so will be used effectively in the surgical operation without having to proceed with other dosing operations.

Figure 14:
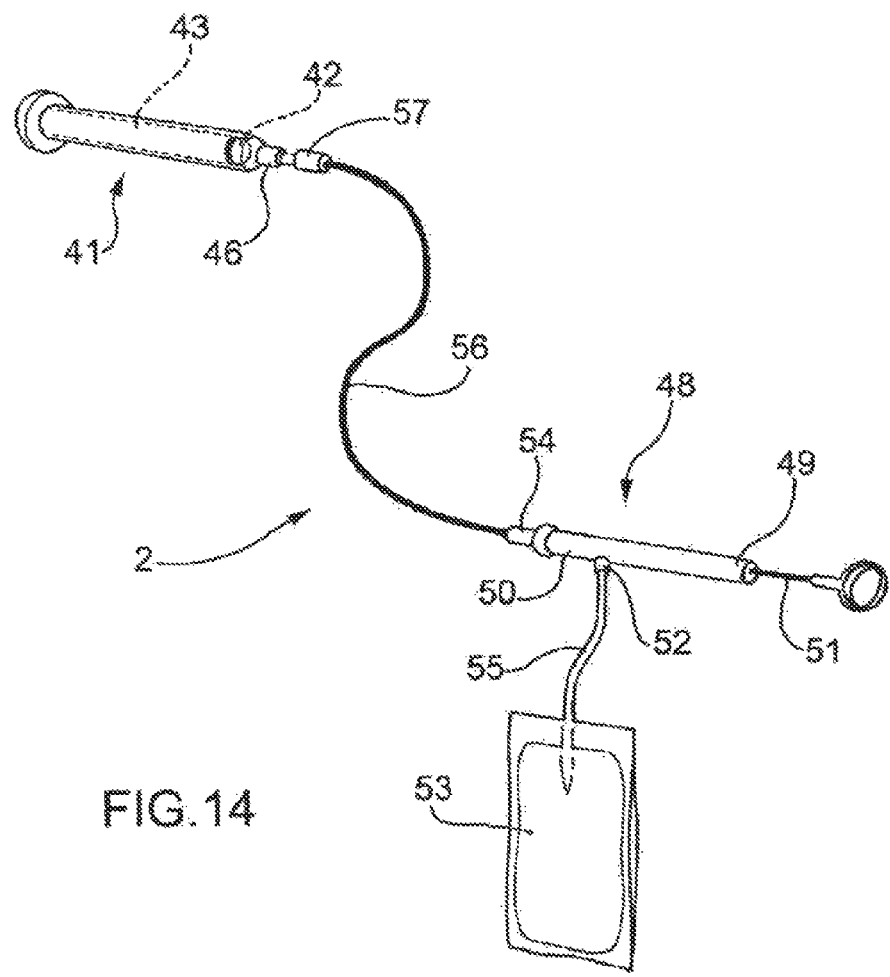
FIG. 14 represents a perspective view of the dispensing unit of the mixer according to the invention, in another form of embodiment.
Figure 15:
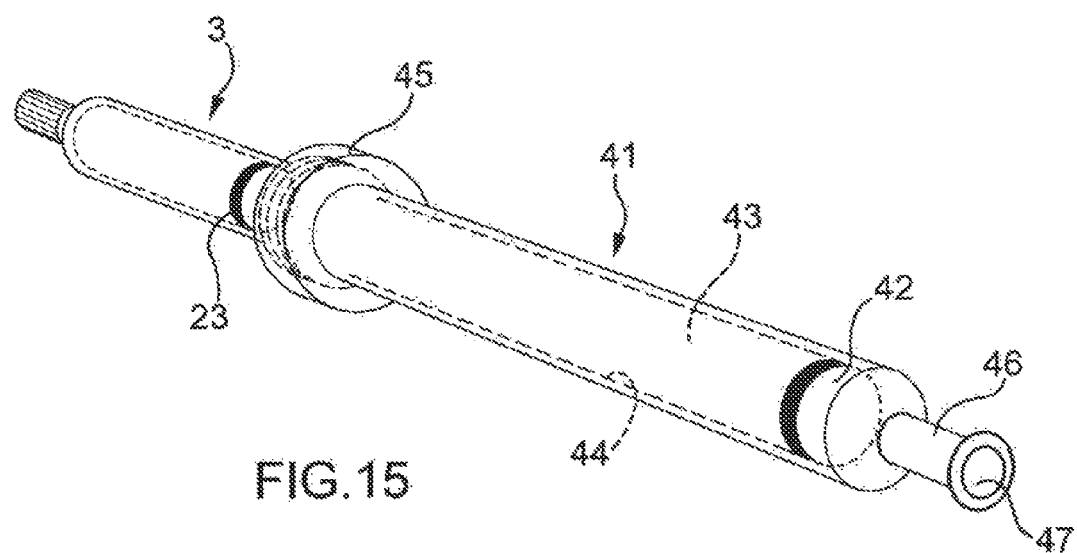
FIG. 15 shows a perspective view of a detail of the dispensing unit of FIG. 14, coupled to the mixing unit.

In another form of embodiment of the mixer according to the invention, represented in FIGS. 14 and 15, the mixing unit 3 comprises a container 24 which is substantially in the shape of a syringe, defining the mixing chamber 21 and in which the compound can be prepared using the cartridge 4 as explained in the previous forms of embodiment.

With particular reference to FIG. 14, the dispensing unit 2 of the compound comprises, in this current form of embodiment a drive element 41 for the piston 23 of the mixing unit 3 which can be remotely started, as will be made clearer further on. Such remote starting considerably reduces exposure of the operators to any radiation there may be in the area where the surgical operation is being performed.

The drive element 41, represented in detail in FIG. 15 associated with the mixing unit 3, comprises a syringe element inside which a drive piston 42 slides in a hermetically sealed way, connected to a respective axial drive stem 43: the drive piston 42 defines, together with the sides of the syringe element, a drive chamber 44. On one of its ends, the drive element 41 comprises a threaded opening 45 that connects to the mixing unit 3 while on the other end it comprises a tang 46 with an axial hole 47 allowing the drive chamber 44 to communicate with the outside.

The dispensing unit 2 also comprises pumping means, indicated with 48, of a thrusting fluid for the drive piston 42: these pumping means 48 are suitable for making the drive stem 43 move in such a way that it presses the piston 23 of the mixing unit 3 and dispenses the compound during the surgical operation. The use of the above mentioned pumping means 48 allows the command and the control of the compound dispensing to be located remotely so that the operators are in an area protected against radiation.

The pumping means 48 comprise a hand pump 49 composed of a cylindrical chamber 50 inside which a manually operated plunger 51 slides. The cylindrical chamber 50 has a first fitting 52 which communicates with a tank 53 of fluid and a second fitting 54 which is coaxial to the cylindrical chamber 50.

The tank 53 is composed of a disposable bag made in a known type of plastic material, containing a sterile physiological solution; a first pipe 55 connects the tank 53 to the first fitting 52 in a unidirectional way by means of, e.g., a check valve of the known type and not shown in the figures.

A second pipe 56, of an appropriate length, connects—in a unidirectional way by means of, e.g., a check valve of the known type and not shown in the figures—the second fitting 54 to a third fitting 57 mounted by the tang 46 of the drive element 41.

The way in which the mixer is used according to this form of embodiment is the following.

Once the compound has been prepared with the mixing unit 3, according to the procedures described above, the mixing unit 3 is connected, in a sealed way, to the opening 45: in this way the end of the drive stem 43 is moved into contact with the piston 23 of the mixing unit 3.

Then, by means of the hand pump 49, the plunger 51 is pulled towards the outside so the physiological solution can go from the tank 53 into the cylindrical chamber 50 through the first pipe 55. Subsequently, by exerting pressure on the plunger 51, the physiological solution flows through the second pipe 56 so that the solution, having reached an appropriate pressure, makes the drive piston 42 move with the relative drive stem 43; in this way we have a thrusting action on the piston 23 of the mixing unit 3 which dispenses the compound inside, e.g., a syringe like the one described previously, or other means and/or devices provided for carrying out the operation and which are not the object of this invention.

Figure 16:
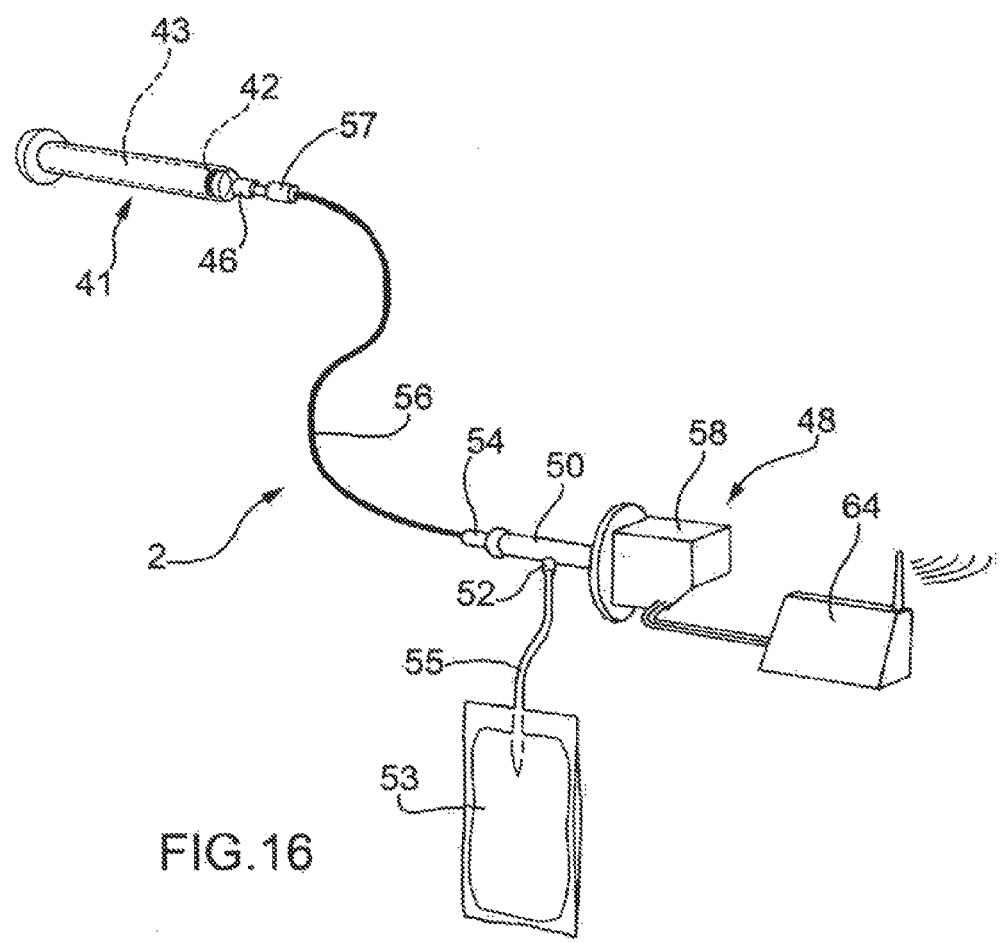
FIG. 16 illustrates a perspective view of the dispensing unit of the mixer according to the invention, in another form of embodiment.
Figure 17:
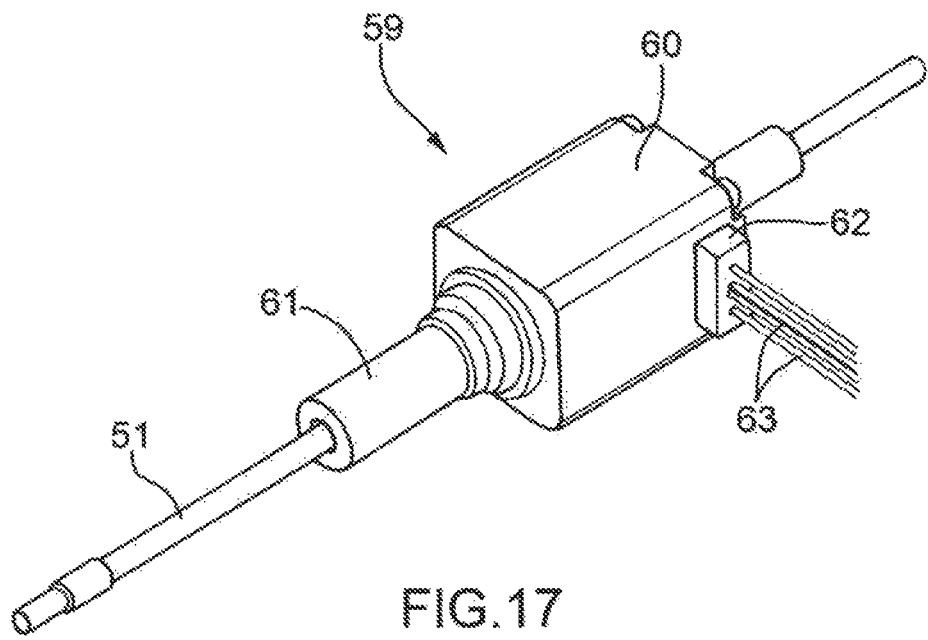
FIG. 17 represents a perspective view of the electromechanical actuator of the dispensing unit of FIG. 16.

Yet another form of embodiment of the mixer according to the invention is represented in FIGS. 16, 17.

In this form of embodiment, the pumping means 48 of the physiological solution, introduced in the previous form of embodiment, comprise a remotely controllable electromechanical pump 58 which requires no manual work by the operators. More in detail, this electromechanical pump 58 comprises a cylindrical chamber 50 similar to the one described in the previous form of embodiment, i.e. having a first communicating fitting with a first pipe 55 and a second communicating fitting 54 with a second pipe 56. A hermetically sealed plunger 51 slides inside the cylindrical chamber 50, the plunger 51 being associated with an electromechanical actuator 59, represented in detail in FIG. 17 and which, in turn, is fixed to the cylindrical chamber 50. The electromechanical actuator 59 comprises an electric motor 60 coupled to a screw mechanism of the type known, that acts on the plunger 51 which slides inside a cylindrical guide 61 integral with the motor 60.

The motor 60 has a terminal 62 for the electrical connection, via cables 63, to a receiving station 64 of radio control signals emitted by a transmitting station, not represented in the figures but of the type known, and which is remotely operated by the operators. As mentioned previously, the first fitting 52 connects the cylindrical chamber 50 to a tank 53 of physiological solution, while the second fitting 54 hydraulically connects the cylindrical chamber 50 to the third fitting 57 on the drive element 40, already described.

This technical solution allows control of the pumping means 48 to be transferred to any position protected against the radiations there could be in the room and, in addition, does not require the manual operation of the above mentioned means 48.

Another form of embodiment envisages one dispensing unit 2 of the compound comprising a drive element 41 that can be started remotely, suitable for exerting a thrust of pressure on the piston 23 of the mixing unit 3 so the compound can be dispensed.

More in detail, the dispensing unit 2 comprises an electromechanical actuator of the type similar to the one illustrated in FIG. 17, interlocked to a receiving station like the one shown in FIG. 16. The plunger 51 of the electromechanical actuator 59 can be connected mechanically to the drive piston 42 so that, subsequent to a suitable command signal received from a transmitting station, the drive stem 32 of the drive element 41 can press on the piston 23 and thus dispense the compound.

This invention has been described according to preferred forms of embodiment but equivalent variants can be conceived without falling outside the protection scope of these claims.

The invention claimed is:
1. A mixer for biphasic compounds, comprising:
a chamber for containing a solid phase delimited, at one end, by a channel and, at the other end, by a piston sealing said chamber;
a stem insertable within the chamber, said stem comprising a wall having an exterior surface and defining an axial cavity and configured to press on said piston in order to dispense said biphasic compound;
a stirrer comprising a longitudinal rod slidably inserted within said axial cavity of said stem; and
a cartridge containing a phial of a liquid phase, said chamber and said cartridge are able to communicate through said channel of said chamber in a sterile manner, wherein said cartridge comprises an external casing made in a deformable material and said phial is of the breakable type, wherein said phial is broken from the outside on a breaking point.

2. The mixer according to claim 1, wherein said casing is made in a flexible material.

3. The mixer according to claim 1, wherein said casing has an internal volume greater than the volume taken up by said phial.

4. The mixer according to claim 1, wherein said stirrer is in the shape of a propeller.

5. The mixer according to claim 1, wherein said rod comprises a gripping knob.

6. The mixer according to claim 1, wherein said chamber and said cartridge can be connected through screw means.

* * * * *